United States Patent
Kim et al.

(10) Patent No.: US 9,221,733 B2
(45) Date of Patent: Dec. 29, 2015

(54) METHODS AND SYSTEMS USEFUL FOR DRYING ETHANOL

(71) Applicants: Purdue Research Foundation, West Lafayette, IN (US); Archer Daniels Midland Company, Decatur, IL (US)

(72) Inventors: Youngmi Kim, Woodbury, MN (US); Richard L. Hendrickson, West Lafayette, IN (US); Nathan Mosier, West Lafayette, IN (US); Michael R. Ladisch, West Lafayette, IN (US); Ahmad K. Hilaly, Forsyth, IL (US)

(73) Assignees: Purdue Research Foundation, West Lafayette, IN (US); Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 13/966,843

(22) Filed: Aug. 14, 2013

(65) Prior Publication Data

US 2014/0141480 A1 May 22, 2014

Related U.S. Application Data

(63) Continuation of application No. PCT/US2012/025042, filed on Feb. 14, 2012.

(60) Provisional application No. 61/442,524, filed on Feb. 14, 2011.

(51) Int. Cl.
*B01D 53/02* (2006.01)
*C07C 29/76* (2006.01)
(Continued)

(52) U.S. Cl.
CPC .......... *C07C 29/76* (2013.01); *B01J 20/28004* (2013.01); *B01J 20/28019* (2013.01);
(Continued)

(58) Field of Classification Search
CPC .... C07C 29/76; C07C 31/08; B01J 20/28004; B01J 20/28019; B01J 20/28059; B01J 20/3433; B01J 20/3458; B01J 2220/4825; C12P 7/06; Y02E 50/17
See application file for complete search history.

(56) References Cited

U.S. PATENT DOCUMENTS 2,144,333 A 1/1937 Hagen
2003/0104587 A1* 6/2003 Verser et al. .................. 435/135
(Continued)

OTHER PUBLICATIONS
Quintero et al. "Ethanol Dehydration by Adsorption with Starchy and Cellulosic Materials"; Ind. Eng. CHem. Res. 2009, 48, 6783-6788.*
(Continued)

*Primary Examiner* — Christopher P Jones
(74) *Attorney, Agent, or Firm* — Woodard, Emhardt, Moriarty, McNett & Henry LLP

(57) ABSTRACT

Mixtures of ethanol and water are dehydrated using starch pearls to adsorb and remove water. Vapor-phase adsorption equilibrium capacities of cassava starch pellets (tapioca pearls) having different particle sizes are disclosed, and tapioca pearl particles are shown to be surprisingly more effective for dehydrating 88 to 97% w/w feed ethanol than corn grits. The adsorption equilibrium curve and BET surface area measurement show that the adsorption capacity of tapioca pearls is a function of surface area available to water molecules. SEM images demonstrate that the particle architecture required for the adsorption and dehydration properties is that of a core-shell configuration with pre-gel starch acting as a central scaffold holding together other particles to the outer layer of the particle. The outer surface area of the pearls, populated with dry starch granules, is the main factor determining the adsorption capacity of the pearls. Tapioca pearls are shown to possess a surprisingly higher adsorption capacity than corn grits of the same particle size. Pearls of 2 mm size in diameter gave 34% higher linear adsorption equilibrium constant (K) than grits of 1.7 mm.

32 Claims, 9 Drawing Sheets

Process schematic for adsorption apparatus.

(51) Int. Cl.
*B01J 20/28* (2006.01)
*B01J 20/34* (2006.01)
*C12P 7/06* (2006.01)

(52) U.S. Cl.
CPC ........ *B01J20/28059* (2013.01); *B01J 20/3433* (2013.01); *B01J 20/3458* (2013.01); *C12P 7/06* (2013.01); *B01J 2220/4825* (2013.01); *Y02E 50/17* (2013.01)

(56) References Cited

U.S. PATENT DOCUMENTS

| | | |
|---|---|---|
| 2006/0005285 A1 | 1/2006 | Strissel et al. |
| 2006/0008791 A1 | 1/2006 | Kubota et al. |
| 2006/0032935 A1 | 2/2006 | Matsuura |
| 2006/0040024 A1 | 2/2006 | Srinivasan et al. |
| 2006/0047068 A1* | 3/2006 | Doane et al. ............ 525/54.3 |
| 2007/0088182 A1* | 4/2007 | Hilaly et al. ............ 568/916 |
| 2008/0261807 A1* | 10/2008 | Chevigny et al. ............ 502/402 |

OTHER PUBLICATIONS

Cassava-Based Adsorbent for Removing Water from Ethanol Vapor, Chemical Engineering, Suranaree University of Technology, 111 University Ave, Tambon Suranaree, Muang, Nakhorn Ratchasima, 30000 Thailand.

Christianson, D.D. et al., "Correlation of Microscopic Structure of Corn Starch Granules with Rheological Properties of Cooked Pasts," Journal of Food Structure, vol. 1, No. 1, Article 3, 1982.

Ladisch, Michael R., "Biobased adsorbents for drying of gases," Enzyme and Microbial Technology 20:162-164, 1997.

Lee, Jay Y., et al. "Water and Ethanol Sorption Phenomena on Starch", AIChE Journal, Aug. 1991;vol. 37, No. 9, p. 1187-1195.

Xu, Ansui et al., "Structure of Tapioca Pearls Compared to Starch Noodles from Mung Beans", Ceral Chem. 70(4):463-470, 1993.

Youngmi Kim, et al., "Cassava Starch Pearls as a Desiccant for Drying Ethanol", Ind. Eng. Chem. Res. 2011, 50, 8678-8685.

* cited by examiner

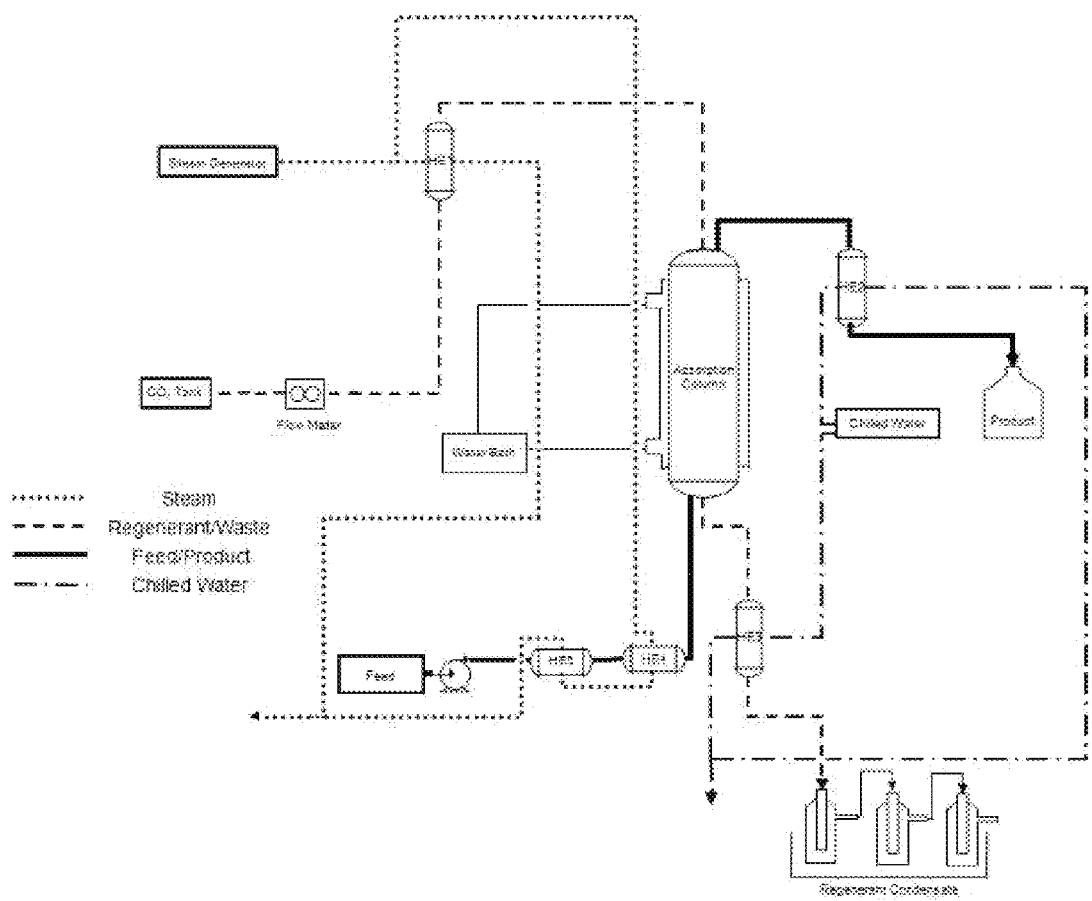
FIG. 1. Process schematic for adsorption apparatus.

METHODS AND SYSTEMS USEFUL FOR DRYING ETHANOL

REFERENCE TO RELATED APPLICATION

The present application is a continuation of International Application Serial No. PCT/US2012/025042, filed Feb. 14, 2012, which claims the benefit of U.S. Provisional Patent Application Ser. No. 61/442,524 filed Feb. 14, 2011, each of which is hereby incorporated herein by reference in its entirety.

TECHNICAL FIELD

The present disclosure relates to the field of dehydrating ethanol distilled from fermentation media, more specifically to use of spherically shaped starch particles as an effective and inexpensive method of dehydrating ethanol, and in certain aspects to the use of pearl starch particles (exemplified by tapioca pearl from cassava) having a particular morphology that makes them effective dehydrating agents.

BACKGROUND

The combination of a conventional distillation process with an appropriate adsorption system to dry ethanol reduces overall energy requirements in producing fuel-grade ethanol[1-3]. Adsorption processes break the ethanol-water azeotrope and remove final amounts of water. Starch-based adsorbents have been proven as an energy-efficient desiccant to remove water from alcohols with advantages of low cost, selectivity for water molecules, and mild regeneration conditions[4-8]. The mechanism of water adsorption by starch is based on the formation of hydrogen bonds between water molecules and hydroxyl groups on the starch. The first industrial use of corn grits as starch based adsorbent was a result of joint effort between Purdue University and Archer Daniels Midland (ADM) in 1984. Unlike commercial inorganic adsorbents such as molecular sieves or silica gels, corn grits are biologically based, biodegradable, non-toxic and derived from renewable biomass. In addition, the spent adsorbent itself can also serve as feedstock for producing ethanol.

Dehydration of 92 to 93% (by weight) ethanol to yield fuel-grade ethanol (99.5% ethanol by weight) on an industrial scale is done by using a fixed bed adsorption system. Water is selectively removed from a hydrous ethanol vapor by corn grits during the adsorption cycle and the corn grit bed is regenerated by hot $CO_2$ gas (~96° C.) that is counter-currently passed through the bed during regeneration. The system consists of two or more packed adsorption beds, of which one is under adsorption mode while at least one other is in regeneration mode. Heat of water adsorption given off during the feed cycle is stored in the bed and used to dry the bed during the regeneration cycle. Other types of regenerant gas, such as nitrogen, could be used for the bed regeneration, but $CO_2$, which is a co-product of ethanol fermentation, is chosen as it is readily available from an ethanol plant[9].

There have been extensive studies on the equilibrium and kinetic aspects of water removal by various types of starch adsorbents at a laboratory scale. The starch adsorbents studied include native corn grits[10,11], modified corn grits[12], corn meal[5,6,13-15], wheat flour[16], synthesized starch-based adsorbent[17], and cassava (manioc) starch pellets[18]. The mechanism of water adsorption, equilibrium kinetics and chemistry of maize-derived starch particles, such as corn grits and corn meal, as desiccants are discussed in many literatures. However, little is known about the capacity of cassava starch for use as a drying agent. The application of cassava starch generally as an adsorbent for water in alcohol mixtures was first reported by Carmo et al. (2004)[18]. They have shown the effectiveness of cassava starch on the liquid phase adsorption of water from various alcohol-water mixtures. The results demonstrated a high affinity for cassava starch to absorb water from various alcohols. However, adsorptive ethanol drying in industry is usually carried out under hot, vapor phase conditions that can alter the properties of starch absorbing particles.

Cassava starch is the fourth largest source for starch production after corn, wheat, and potato[19], and is abundantly produced in various tropical regions. Its world production is approximately 192 million tons per year[22].

It would therefore be beneficial to discover whether any forms of cassava starch might be particularly useful alternatives to corn grits for industrial scale dehydration of ethanol. In addition, it would be further beneficial to define the structural morphology of the fraction of cassava starch particles that conveys the most effective drying properties so as to be able to form starch particles from other sources having that morphology. The present disclosure provides such a discovery as well as a description of the forms of starch and methods of using the same that are particularly suitable for dehydrating ethanol made by fermentation.

SUMMARY

Disclosed herein in certain aspects are methods of dehydrating an ethanol water mixture. In certain aspects the methods include (a) contacting an ethanol:water mixture of at least 80% w/w ethanol with a first end of a column containing a bed of spherically shaped pearled starch particles; and (b) removing a dehydrated ethanol product of at least 99% ethanol from a second end of the column. In one embodiment, the pearled starch particles have a nominal diameter of 0.1-4 mm and have a surface that is at least partially gelatinized and that includes a regular distribution of crystalline starch granules nominally 2-15 microns in diameter over the surface. In another embodiment, the pearled starch particles have a nominal diameter of 0.2-3 mm and have a surface that is at least partially gelatinized and that includes a regular distribution of crystalline starch granules nominally 5-10 microns in diameter over the surface. The method may further include regenerating the bed of pearled starch particles in the column by contacting the second end of the column with $CO_2$ heated to at least about 105° C. and collecting water and residual ethanol from the first end of the column.

In typical embodiments, the bed of spherically shaped pearled starch particles has a water content of 10% or less prior to being contacted by the ethanol:water mixture. In certain beneficial embodiments the ethanol:water mixture is in a vapor phase when contacting the bed of spherically shaped pearled starch particles. Typically, the bed of spherically shaped pearled starch particles has a temperature of 90-110° C. when the ethanol:water mixture is contacted with the bed. Also typically the ethanol:water mixture is in a vapor phase at a temperature of about 100 to 110° C. when contacting the bed of spherically shaped pearled starch particles.

One embodiment of suitable spherically shaped pearled starch particles can be characterized as having a BET surface area of 0.4-0.6 $m^2/g$. Also, the spherically shaped pearled starch particles can be characterized as having an equilibrium absorption capacity of 6.5-12.5 mg/g, for ethanol and 25-27 mg/g for water. Typically, the spherically shaped pearled starch particles have a nominal diameter of 0.5 to 1 mm.

In a particular embodiment, the spherically shaped pearled starch particles are tapioca pearl starch particles. In another particular embodiment, the spherically shaped pearled starch particles are corn pearl starch particles.

Another aspect provides a method of dehydrating an ethanol water mixture that includes, contacting an ethanol:water mixture of 88-97% w/w ethanol with a first end of a column bed consisting of spherically shaped pearled starch particles; and, removing a dehydrated ethanol product being at least 99% ethanol from a second end of the column. In one embodiment, the starch particles are selected to have an average nominal diameter of 0.1-4 mm and the starch particles are characterized as having (i) at least one of a gelatinized or gelatinized and retrograded starch core, and (ii) the core being surrounded by an aggregate of crystalline starch granules nominally 2-15 microns in diameter. In another embodiment, the starch particles are selected to have an average nominal diameter of 0.5-1 mm and the starch particles are characterized as having (i) at least one of a gelatinized or gelatinized and retrograded starch core, and (ii) the core being surrounded by an aggregate of crystalline starch granules nominally 5-10 microns in diameter.

Again, in typical embodiments, the spherically shaped pearled starch particles are tapioca pearl starch particles or in other embodiments may be corn pearl starch particles.

Another aspect relates to a method of making the starch particles. A typical method involves, obtaining a source of starch having at least 80% amylopectin and dried to a moisture content of about 10% or less; grinding the starch source to form at least a first fraction containing irregularly shaped starch particles having a diameter of 0.5 to 3 mm; heating and simultaneously tumbling the first fraction of irregularly shaped starch particles for a time and at a temperature sufficient to form a second fraction of spherically shaped starch particles having at least a partially gelatinized surface surrounded by an aggregate of crystalline starch granules; and selecting a third fraction of starch particles from the second fraction. In one embodiment, the crystalline starch granules have a nominal diameter of 2-15 microns, and the third fraction is selected to have a diameter of about 0.1 to about 4 mm. In another embodiment, the crystalline starch granules have a nominal diameter of 5-10 microns, and the third fraction is selected to have a diameter of about 0.2 to about 3 mm.

In another aspect, the present invention provides a method for dehydrating a mixed vapor containing ethanol and at least 3% by weight water. The method includes contacting the mixed vapor with spherically shaped starch particles at a temperature in the range of about 90° C. to 120° C. under conditions effective to dehydrate the mixed vapor to produce an ethanol vapor constituted at least 99% by weight ethanol. The ethanol vapor is condensed to produce a liquid product constituted at least 99% by weight ethanol. In one embodiment, the spherically shaped starch particles have an average nominal diameter of about 0.1 to about 4 mm. In another embodiment, the spherically shaped starch particles have an average nominal diameter of about 0.2 to about 3 mm.

In another aspect, provided is an apparatus useful for dehydrating a mixed vapor containing ethanol and water. The apparatus includes a column defining an internal volume. A bed of spherically shaped starch particles is located in the internal volume of the column, and the particles can have an average nominal diameter of about 0.1 to 4 mm, or about 0.2 to about 3 mm. The apparatus can also include a vapor feed line fluidly coupled to the column, and/or means for heating the bed of particles in the column, and/or a regeneration gas feed line fluidly coupled to the column.

In another aspect, the invention provides a method for producing ethanol that includes fermenting a medium to produce an aqueous fermentation broth containing ethanol and water. Any of a variety of well known methods can be used for such a fermentation. The fermentation broth is distilled to produce a mixture containing ethanol and water; and the mixture is dehydrated by contacting a vapor of the mixture with starch pearls so as to adsorb water on the starch pearls.

In still further aspects, the invention provides uses of starch pearls in the dehydration of mixtures containing water and ethanol, and starch pearls for use in such dehydration processes.

In embodiments described herein the source of starch may be cassava or may be another source such as corn, or may be a mixture of sources. Starch particles made by this method are useful in the forgoing method to dehydrate an ethanol:water vapor containing 85 to 97% ethanol by weight. Additionally, in embodiments described herein, the ethanol:water mixture to be dehydrated can be derived from the fermentation of a fermentation medium by microorganisms (e.g. yeast) to produce a fermentation broth. Typically, this fermentation broth is first distilled to produce an ethanol:water mixture. This mixture can then be subjected to dehydration processing as described herein. The mixture containing ethanol and water for processing herein may also be derived from other sources, for example from food or pharmaceutical processing operations that use ethanol and produce wet ethanol waste streams. Such waste streams can be dehydrated as described herein to produce a dessicated ethanol product that can be recycled in the processing operation. Further, in embodiments described herein that involve methods for the dehydration of mixtures containing ethanol and water using starch pearls, the methods can be conducted under conditions that are effective to provide a water:ethanol equilibrium separation factor of greater than 35, for example in certain embodiments in the range of about 35 to about 70.

Still further embodiments and associated features and advantages will be apparent from the descriptions herein.

BRIEF DESCRIPTION OF THE FIGURES

FIG. 1 shows a process schematic for an adsorption apparatus used in an exemplary study of the present invention.

DETAILED DESCRIPTION

Figure 2A:
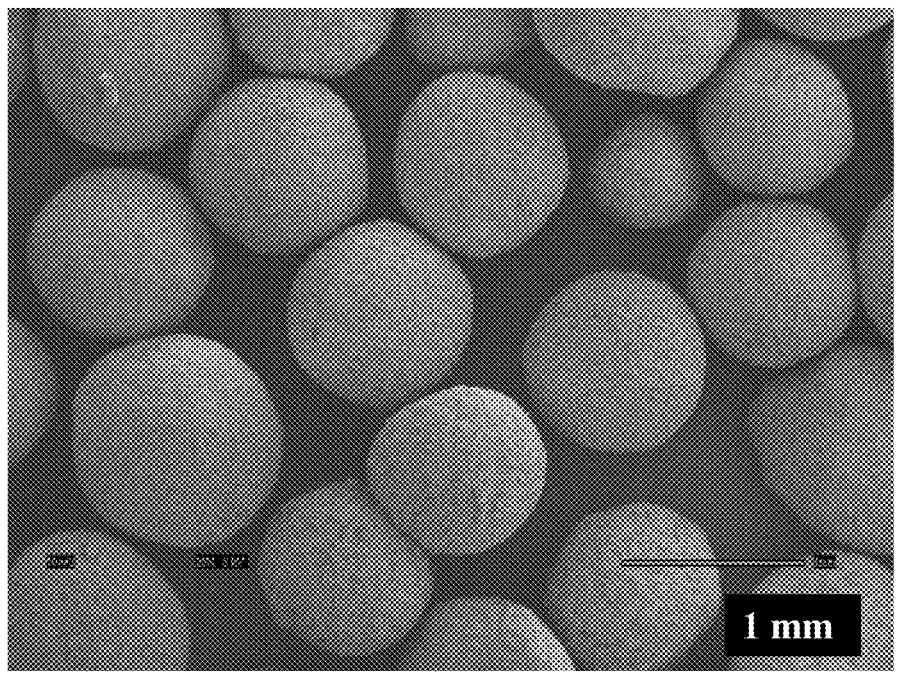
FIGS. 2A-2F show digital images of Scanning Electron Microscopy (SEM) images of cassava starch spherical pellets. (2A) 1 mm particle, ×20 mag..; (2B) surface of 2 mm particle, ×500 mag.; (2C) surface of 1 mm particle, ×500 mag.; (2D) surface of 0.5 mm particle, ×300 mag.; (2E) (2F) inside of 1 mm particle, ×300 mag.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed, in certain embodiments, the present invention provides methods, apparatuses and systems that can be useful in removing water from a mixture containing ethanol and water. These embodiments can involve the use of starch pearls and in particular aspects the contact of a feed vapor containing an ethanol-water mixture with a bed of starch pearls so as to produce a dehydrated ethanol product having a reduced amount of water, e.g. considered on the basis of weight percent, relative to the feed vapor. The feed vapor can be provided by vaporizing a liquid mixture of ethanol and water, and the liquid mixture of ethanol and water can be the product of a fermentation process. In some specific embodiments, the liquid mixture of ethanol and water can be a liquid product obtained by distilling a fermentation broth, or fraction thereof, to produce a liquid distillate containing ethanol and water. Such a liquid distillate can, for example, be composed about 88% to 97% by weight ethanol, and about 12% to about 3% by weight water.

Although exemplified herein with cassava starch, the present disclosure, which is directed toward particular types of starch particles, is applicable to starch from a variety of sources provided the starch source has certain minimal characteristics. Those characteristics are (1) that the starch source has at least 65%, and more preferably at least 75% amylopectin content; (2) the starch has a high enough molecular weight to be capable of forming gelatinized particles of at least 0.2 mm in diameter; and (3) that the starch source is at least 95% and most preferably at least 99% starch. Suitable sources of starch include without limitation, cassava, wheat, corn, sorghum, rice and potato. Cassava starch is preferred.

With regard to the requirements for the starch source, if the amylopectin content is too low, the starch will not adsorb enough water to be a practical substitute for conventional corn grits as a drying agent. If the starch has a low molecular weight, it will be difficult to form into gelatinized (or partially gelatinized) spheres of at least 0.2 mm and will have too low of a BET surface area (described herein after). If the starch is contaminated with non-starch material such as fiber (e.g., pericarp fragments), protein (e.g., zein or other storage proteins), or oils (e.g., germ fragments) it will not form spherical particles having a uniform distribution of crystalline granules as described herein after and the non-starch material will partially interfere with the flow and absorption characteristics of the drying bed. For purposes of comparison, although the starch in corn grits has a high enough molecular weight and sufficient amylopectin content, the grits themselves are crudely separated endosperm particles that are dried and ground—typically obtained from a corn dry milling operation. The grits therefore contain residual fiber and oil components. However, if the starch fraction of the endosperm is purified, for example, as typically occurs in a corn wet milling operation where the pericarp, protein and germ fractions are efficiently removed from the starch, the purified corn starch would be just as suitable a source for making the particles exemplified herein with cassava starch formed into pearls.

The main component of cassava starch, like other starches, is amylopectin which comprises nearly 80% of total starch[20,21]. Spherical particles of cassava starch, which are generally referred to as "tapioca pearls", are commercially available as food additives. The inventors have defined a fraction of some commercially available tapioca pearls for food applications that have a spherical shape, hardness, and particular surface agglomerated morphology within a size range that present a particularly useful replacement for corn grits as an alcohol desiccant. The defined particle size and morphology along with the fact that commercially available tapioca pearls are generally free of dusty particles are also makes them advantageous for modeling desiccation processes.

Cassava starch in the form of tapioca pearls exemplifies a form of starch particles particularly suitable for use as a desiccant for dehydration of ethanol under vapor phase conditions. The properties of tapioca pearls that make them particularly suitable as an alcohol desiccant can be applied to make pearled starch particles having similar utility from any suitable starch source as described herein before. For purposes of clarity and consistency of use the term "particle" in reference to starch is a discretely observable agglomeration of a mass of starch that is greater than 100 microns in diameter. The particle is typically an agglomeration of starch granules. A "granule" is a discretely observable smaller mass of starch that is typically spherical in appearance and less than 100 microns in diameter. The term "pearled starch" or "starch pearls" refers to generally spherical or spheroid particles comprised of agglomerated starch granules. Starch pearls can be provided by starch that has been rolled into spherically shaped particles by one or more tumbling or agitation processes, dried, and subjected to heat for a time sufficient to at least partially gelatinize at least a portion of at least the surface of the starch particle and then cooled, forming a hardened spherical particle of 0.2 to 3 mm diameter having a regular distribution of crystalline starch granules of 5-10 microns on the at least partially gelatinized surface; or, in other aspects forming a hardened spherical particle of 0.1 to 4 mm diameter having a regular distribution of crystalline starch granules of 2-15 microns on the at least partially gelatinized surface. The term "spherically shaped" or "spheroid" means generally having a ball shaped appearance when viewed under low magnification, as illustrated for example, in FIG. 2A. Starch pearls or other particles comprised of agglomerated starch granules for use in the invention are preferably comprised at least about 75% by weight of starch, more preferably at least about 90% by weight of starch, and most preferably essentially all starch, e.g. about 98% to 100% by weight of starch. When a material(s) other than starch is present it/they may for example be other plant material, fillers or other substances to aid or modify the properties of the starch pearls. The population of starch pearls or other agglomerate particles can also have a substantially uniform maximum particle dimension (e.g. diameter), for example with about 75% or more of the particles in the population having a maximum particle dimension within 20% of the average maximum dimension of the population, with this figure more preferably being about 90% or more.

In exemplary studies described herein, selected cassava pearl fractions with different diameters and corn grits were tested and compared in terms of adsorption capacity and selectivity for water under identical operating conditions. The results provide an understanding of the properties and structural characteristics that make pearled starch particles particularly useful in comparison to corn grit starch particles for use as an alcohol drying desiccant, especially ethanol. This understanding is applicable to pearled starch particles that may be made from alternative sources that would have similar superior performance properties as demonstrated by tapioca pearls. Such starch particles are useful for at least partially removing water from an ethanol water vapor mixture of at least 80% ethanol, at least 85% ethanol, at least 90% ethanol, at least 95% ethanol or at least 97% ethanol. In a typical practice, an ethanol water vapor mixture of at least 97% can be desiccated to form an ethanol product that is fuel grade, which is at least 99.5% ethanol.

A regenerant gas, such as carbon dioxide, nitrogen or air, can be used to remove water from the starch pearls after their use in a dehydration process e.g. as described herein. In certain embodiments, ethanol vapors from a dehydrated ethanol product of a previous dehydration process using the starch pearls can be used alone or in combination with another gas, to regenerate the starch pearls in between dehydration processes.

A better understanding of the present invention may be gleaned from a description of the materials and methods used to provide the data described in the following Experimental.

EXPERIMENTAL

Cassava (tapioca) pearls having a nominal particle size of 0.6 mm were purchased from Industria Agro Comercial Cassava S/A (Rio do Sul-SC, Brazil). The tapioca pearls were further sieved into fractions of three different mean particle diameters: 2 mm (8-10 mesh), 1.0 mm (18-20 mesh), and 0.5 mm (35-40 mesh). Corn grits having a mean diameter of 1.7 mm were provided by the Archer Daniels Midland Company (Decatur, Ill., USA). Feed solutions were prepared by mixing 200 proof ethanol (Pharmco, Brookfield, Conn.) with deionized water to give various ethanol/water mixtures in the range of 88% to 97% by weight ethanol. All other chemicals were purchased from Sigma-Aldrich (St. Louise, Mo., USA) unless specified otherwise.

Surface and inside images of the tapioca pearl particles were taken with a scanning electron microscope (SEM, Model JEOL JSM-840, JEOL USA Inc., Peabody, Mass., USA) at the Life Science Microscopy Facility at Purdue University. Tapioca adsorbents samples for the SEM imaging were prepared by mounting it on aluminum stubs using double-coated tape. Excess material was gently blown off and the sample was sputter coated with AuPd in the presence of argon gas using a Hummer I sputter coater (Technics Inc., Alexandria, Va.) prior to imaging with the SEM. The BET Surface area of tapioca adsorbents samples with three different particle diameters were measured using a Micromeritics TriStar 3000 at Micromeritics Analytical Services (Norcross, Ga., USA).

The system apparatus used for the data presented herein is shown in FIG. 1 in which the abbreviations "HE" denote heat exchangers. A 6 foot adsorption column constructed from two glass columns (50×1200 mm and 50×600 mm Pyrex Glass Jacketed Chromatography Column, Ace Glass, Vineland, N.J.) were connected to each other giving total length of 180 cm (6 feet). For adsorption equilibrium runs, a 1 ft long mesh screen basket packed with a known particle size of tapioca pearls was inserted into the 6 ft column and the space below was left empty. The dry weight of tapioca pearls packed in the mesh screen basket was approximately 350 g and was 320 g for corn grits. Breakthrough and desorption characteristics of adsorbents being compared were determined using a full 6 ft bed packed with 2.5 kg dry tapioca peals or corn grits.

Initially, the adsorption bed was prepared for experimentation by drying the packed adsorbents for 4 hrs using a regenerant gas flow rate of 7.5 L/min and then overnight at 1.75 L/min using 105° C. dry $CO_2$ gas in a down flow direction. The temperature of the column filled with adsorbents was kept at 90° C. by hot water circulated through a water-jacket. The adsorption column was not only water-jacketed but also insulated using a 2 in×⅛ inch thick ceramic fiber insulation strip (McMaster-CARR, Elmhurst, Ind.) to minimize heat loss during experiments.

During the adsorption cycle, an ethanol/water vapor mixture of a known concentration at 110° C. was passed through the packed bed of adsorbents at a vapor superficial velocity of 0.2 m/s until the packed adsorbents reached equilibrium. The "dry" product stream removed during the feed cycle was condensed in a heat exchanger (HE2) with chilled water. Product composition was monitored on-line through a density meter (Promass 83, Endress+Hauser, Greenwood, Ind.) with accuracy to two decimal places of % wt ethanol to ensure that the packed adsorbents reached equilibrium. The system was regarded to reach equilibrium when there was less than 0.1% change in the product composition within a 5 min increment. Upon completion of the feed cycle, the bed was regenerated with hot $CO_2$ (105° C.) at 5.6 m/min flowing in countercurrent direction to the feed during the adsorption phase. Regenerant condensate was collected through three cold traps immersed in an ice bucket. The regenerant condensate collected at these traps was carefully weighed and the composition analyzed by GC. Bed regeneration was done until there was no increase in regenerant condensate weight. Water and ethanol vapor present in the void space of the bed at the time of regeneration was subtracted from the regenerant condensate. The adsorption capacity of tapioca pearls at equilibrium was calculated and expressed as mg water adsorbed per g of dry tapioca pearls packed in the system. Duplicate runs were made for all experiments unless otherwise noted. After each run, the bed was kept in regeneration mode by flowing 105° C. dry $CO_2$ at 1.75 L/min for at least 12 hrs until the next run is made. Regenerant condensate collected during the 12 hr regeneration was also collected and analyzed. The dryness of the system for the next run was ensured by measuring humidity of the regeneration off-gas using a hygrometer (Humidity and temperature probe HMP368, Vaisala Oyj, Vantaa, Finland). All runs disclosed herein represent data obtained from pre-equilibrated adsorbents with which at least two pre-runs were made. None of the data given herein comes from use of fresh unused adsorbents.

Temperature, pressure, moisture content, flow rate of dry $CO_2$, and mass of feed and product were monitored through a LabVIEW compact field point data acquisition system (National Instruments Co., Austin, Tex.). The masses of feed and product were measured continuously using digital balances. Temperatures of the system were also measured and monitored by thermocouples and temperature transmitters. The flow rate of dry $CO_2$ was monitored and controlled using a mass flow meter/control (Brooks Model 5851S, Brooks Instruments, Hatfield, Pa.). The communication module was a LabVIEW Real-Time/Ethernet Network Module (cFP-2000, National Instruments Co., Austin, Tex.). Software to acquire and manipulate signal data was prepared by VI Engineering (Indianapolis, Ind.).

The ethanol concentration of feed, product, and regenerant condensate was measured using a GC system consisting of a gas chromatography system (Varian 3400 Gas Chromatography, Varian Inc., Palo Alto, Calif.), HayeSep P column (8'×⅛" SS, 60/80 mesh, Hayes Separations, Bandera, Tex.), integrator (Agilent 3395 Integrator, Agilent Technologies, Palo Alto, Calif.), and compressed gas tank containing grade 5 helium, which was utilized as a carrier gas. The amount of sample injected was 2 μL. Temperatures of the column, injection, and detector were 120, 200, 200° C., respectively. Flow rate was 30 ml/min. Each sample analysis was completed in 5 min. Preparation of pearled cassava starch particles generally involved the following steps[23]: granulation of wetted starch into beads, stirring the beads on a hot plate, drying the pearls at 40-60° C. in a stream of hot air to approximately 10% moisture, size selection, and finally cooling and packing according to the pearl size. The process provides a heat-moisture treatment that leads to gelatinization of the starch. Upon cooling, the gelatinized starch is retrograded, a process of at least partial re-crystallization of starch on the surface of the particle so that at least a portion of the surface of the particle may be characterized as at partially gelatinized. The core of the particle is more fully gelatinized having little observable crystalline structure. Commercial tapioca pearls contain approximately 60% gelatinized starch[24]. During the process, starch granules adhere to each other and these elements aggregate onto the outer surface of the particle to form a more or less spherical shape[25].

Figure 2B:
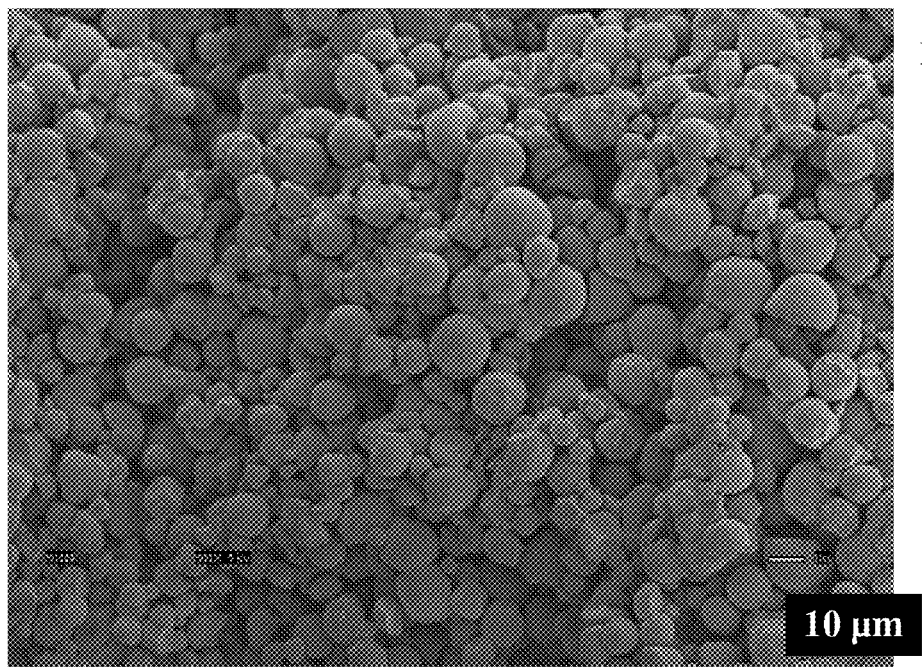
Figure 2C:
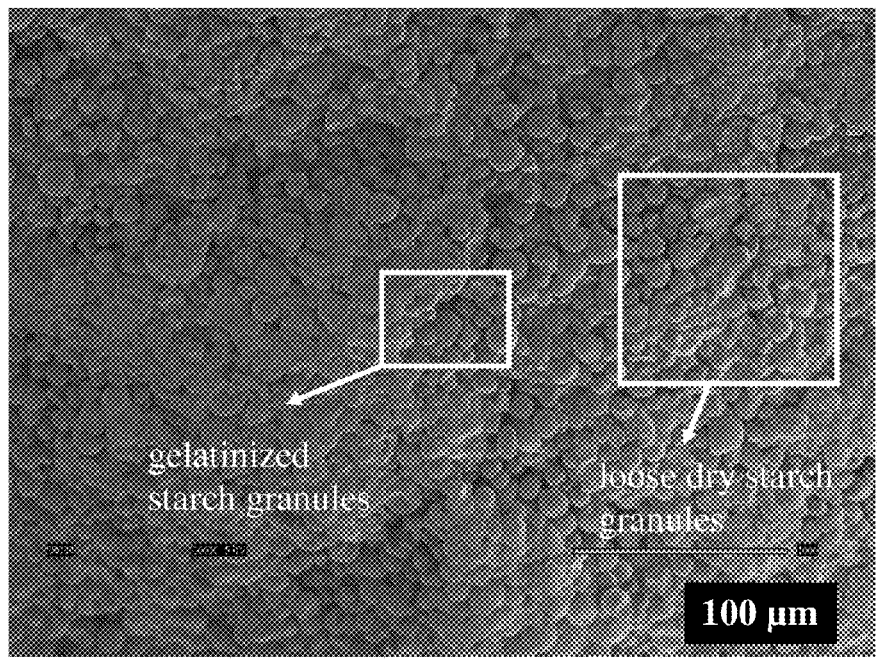
Figure 2D:
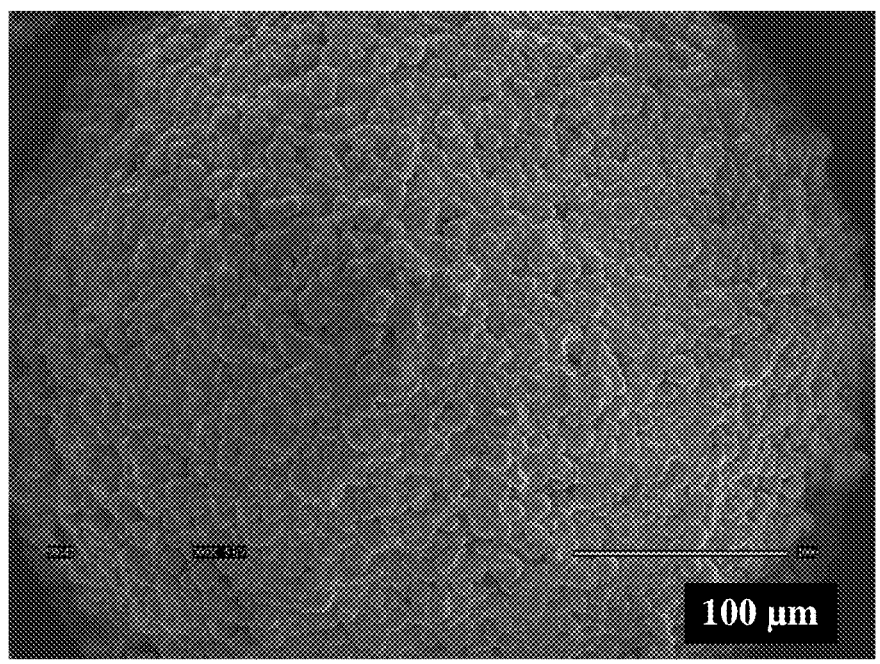

SEM images of cassava tapioca pearls prepared as described herein are shown in FIG. 2A-F. The particles themselves are spherical, as shown in FIG. 2A, and when packed in a column, easily roll down the walls of the column to form what appears to be a well packed bed. The tapioca pearls, even before sieving, are free of dusty particles. The surface of the cassava pearls is heavily populated with starch granules of 5-10 μm diameter as shown in FIG. 2B-D. The surface is, however, not uniformly smooth and homogeneous. While for most of part, particles appear to be densely packed with a regular distribution of distinctive starch granules, some particles of certain sizes have regions that seem smoother than other regions due to gelatinization of the particle and formation of the aggregate of granules. As used herein, "regular distribution" means that visually, the particle surface appears to be mostly evenly coated with the granules.

Figure 2E:
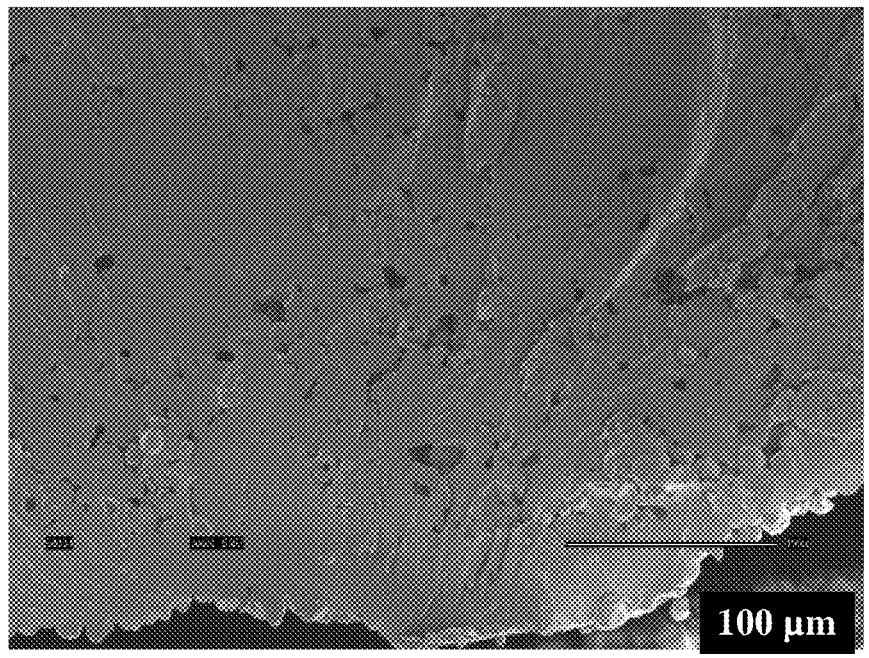
Figure 2F:
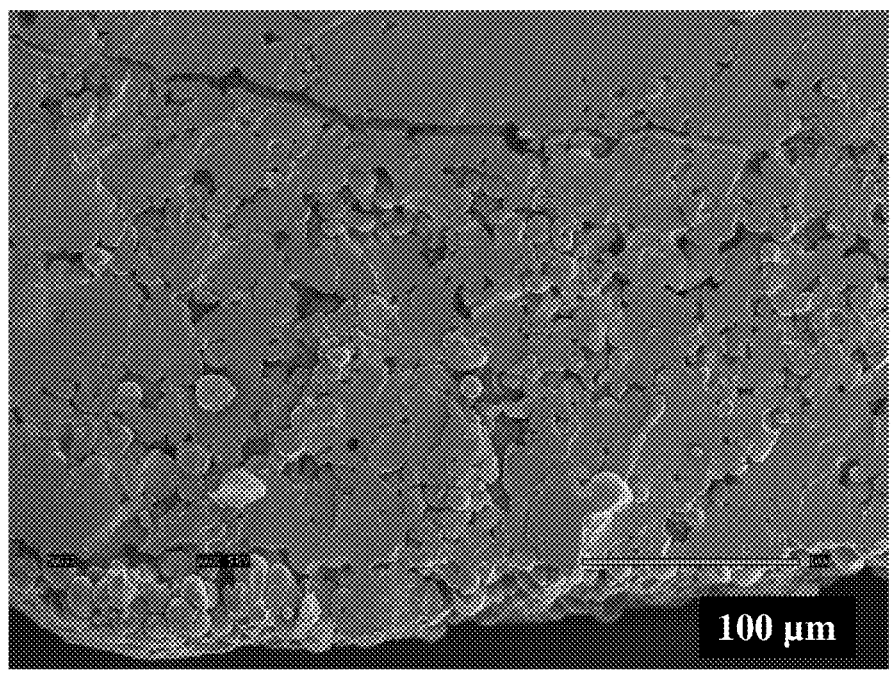

It should be noted that, the surface of 0.5 mm micropearl as shown in FIG. 2D has fewer starch granules and appears to be more gelatinized than the surface of 2 mm pearls, which are shown in FIGS. 2B and 2C. Inside, in the core of the particle beneath the surface, the pearls are extensively gelatinized and have no significant internal pores accessible to water molecules as shown in FIGS. 2E and 2F.

The SEM images of cassava micropearl adsorbents suggest that the particle architecture resembles a core-shell configuration with a gelatinized starch interior and with at least part of the gelatinized surface acting as a scaffold that holds the smaller starch granules to the outer layer of the particle. While not being bound by the theory, the adsorption inside the particle is postulated to be small because as shown in the electron micrographs, the core has few porous regions, and access to the core of the starch particle should be limited because it is more fully gelatinized and is coated by the crystalline granules. It is believed that the primary sites for adsorption are on the surface of the particle, particularly in and through the crystalline granules. Accordingly, the outer surface area of pearls, populated with crystalline starch granules and crystalline retrograded regions, is expected to become the main factor determining the adsorption capacity of the pearls. The BET[38] surface areas of the three different particle size of various selected cassava pearls are summarized in Table 1.

TABLE 1

BET surface area of cassava micropearl adsorbents.

|  | BET surface area (m²/g) |
|---|---|
| $d_p$ = 2.0 mm | 0.418 ± 0.002 |
| $d_p$ = 1.0 mm | 0.563 ± 0.003 |
| $d_p$ = 0.5 mm | 0.516 ± 0.002 |

The pearls of 0.5-2 mm particle size range gave 0.4-0.56 m²/g BET surface area. Starch granules of 10 μm diameter, in comparison, have a BET surface area of 0.72 m²/g[17]. Considering that the pearls have no significant internal pores as shown in SEM images, the BET surface area of the cassava pearls is thought to reflect mainly the external surface of the particles that are densely covered with starch granules. The ratio of specific surface area of two different particle size of perfect non-porous sphere is inversely correlated to the diameter of spheres according to the following equation:

$$\frac{S_1/\rho V_1}{S_2/\rho V_2} = \frac{D_2}{D_1} \quad (1)$$

where $S_1$ and $S_2$=external surface area of sphere 1 and 2; $V_1$ and $V_2$=volume of sphere 1 and 2; $\rho$=density of the sphere; and $D_1$ and $D_2$=diameter of sphere 1 and 2.

Therefore, given that the particles do not have significant internal pore structures that could affect the total specific surface area, it was expected that the 1 mm cassava pearls would have a higher surface area than the 2 mm ones. The surface area of the 1 mm particle size pearls was measured to be 0.56 m²/g which is 35% higher than that of 2 mm pearls. However, the ratio of BET surface area per unit mass of these two different size particles was only 1.3 which is less than it should be for a 2 mm sphere compared to a 1 mm sphere. For a non-porous smooth surface sphere, the ratio of surface area per unit mass of 2 mm sphere to that of 1 mm sphere should be 2, assuming the same density. The unexpected difference in surface area ratio was interpreted to suggest that the 1 mm particle pearls may be less populated with dry separable starch granules due to gelatinization. More smooth and gelatinized regions appeared as the particle size becomes small enough to be close to its pre-gelatinized core.

This was further confirmed from the data for 0.5 mm pearls. Despite being the smallest particle size tested, the BET surface area was slightly less than that of 1 mm beads, which was reflected in the SEM image in FIG. 2D, showing the overall appearance of starch granules aggregated together due to gelatinization on its surface. Though its BET surface area was still larger than that of 2 mm particles by 23%, it was approximately 10% smaller than that of 1 mm particles.

Figure 2G:
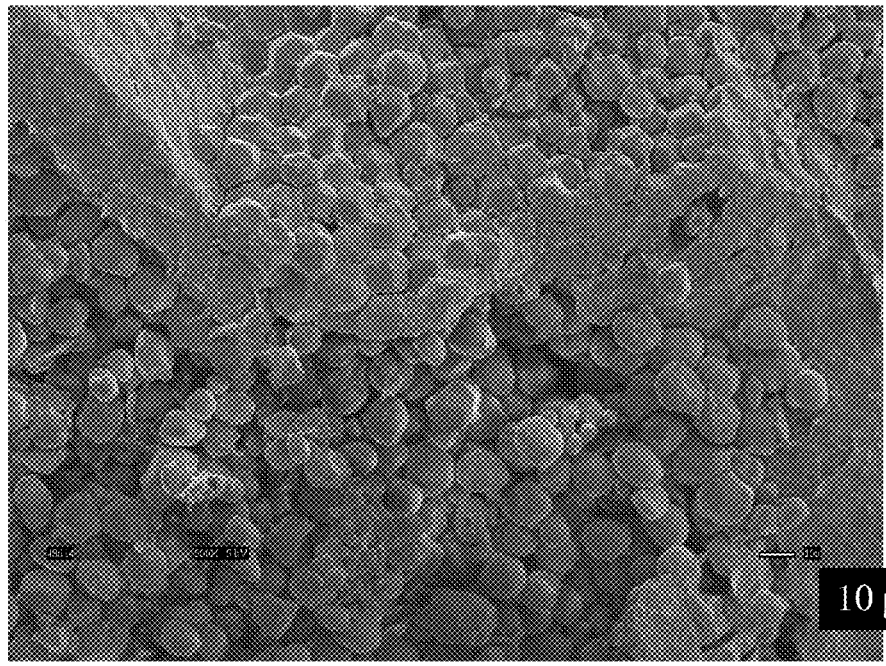
FIGS. 2G and 2H show digital images of SEM images of the surface of corn grits.
Figure 2H:
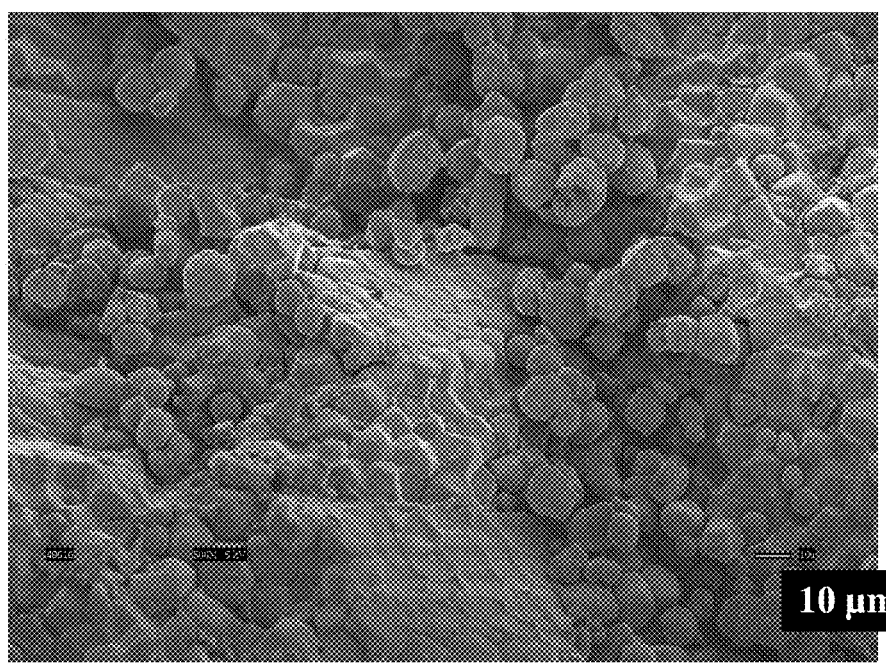

In comparison, SEM images of corn grits are shown in FIGS. 2G and H. The SEM images of corn grit particles revealed that they have a similar surface appearance to cassava pearls. The corn grits surface consisted of smooth vitreous regions and opaque regions of tightly packed spherical starch particles[26,27]. However, the smooth surface on the corn grit particle does not come from cooking (gelatinization) of starch granules. Starch granules in corn grits, especially in horny endosperm of dent corn, are embedded in a honeycomb-like protein matrix[12], which is represented as the smooth surface on the SEM images. Floury endosperm of corn grits, on the other hand, contains more free starch granules that are not tightly aggregated, which are often seen as an opaque region on the corn grit surface. It is known that the ratio of horny to floury endosperm in dent corn is approximately 2:1[12]. As many of starch granules in corn grits are held together by a protein matrix, its external surface area appeared to be much less populated with separable starch granules than cassava pellets (compare FIGS. 2B and 2G, 2H).

Previous studies have shown that only a part of total sorption sites of corn grits is accessible during operation.[10,26] It was hypothesized that the opaque regions with a greater surface area have dominant impacts on determining operational capacity of the corn grits[27]. Water adsorption mainly occurs by the starch granules in this region where water molecules have easy access and can swell the starch matrix upon adsorption. In this sense, efforts were driven to increase surface area per mass of corn grits by creating pores, aiming to enhance operational (non-equilibrium) adsorptive capacity of the adsorbents. The studies have proven that operational adsorption capacity of modified corn grits with a greater surface area is higher than that of unmodified corn grits, despite the lower mass of starch per volume (density) of the modified, highly porous corn grits[12,27,28].

These findings led to our hypothesis that the operational adsorption capacity of cassava pearls would also depend on the surface area of the pearls. The SEM images indicated that the specific surface area might be a major factor on not only the operational adsorption capacity, but also on the equilibrium adsorption capacity of the pearl shaped starch adsorbents. Unlike the corn grits adsorbents, which do not undergo any heat treatment, cassava pearls are pre-cooked and dried resulting in a gelatinized/retrograded core during the manufacturing process. While gelatinization is a process of structural disruption (reduced crystallinity) of starch granules leading to increased water sorption capacity of the starch, cooling of the gelatinized starch leads to retrogradation, a process of gelatinized starch regaining its crystalline form (increased crystallinity) through hydrogen bonding between realigned molecules[29,30]. Thus, gelatinization followed by retrogradation can lead to reduced water adsorption capacity of starch granules due to loss of available hydroxyl group adsorption sites on the starch surface[27]. Because the core of the pearls would have a limited water adsorption capacity, the equilibrium adsorption capacity might also be greatly affected by the outer surface area of the pearls. The relation between surface area and adsorption capacity of cassava pearl adsorbents was therefore further investigated.

Equilibrium Adsorption Capacity of Cassava Pearl-Shaped Adsorbents

The equilibrium adsorption isotherm for the water-starch system is generally well described by type II isotherm for a low relative humidity range[10,11]. Equilibrium behavior of a starch-based adsorbent at a low vapor concentration of water is of particular interest in use of the adsorbent for dehydration of distilled ethanol. Distillation can only give a maximum 95.6% ethanol (w/w), the azeotropic point of ethanol-water mixture. Generally, in current fuel ethanol production process, the dilute fermentation broth resultant of fermenting a medium is concentrated to 85-92% w/w ethanol by distillation. Therefore, the feed concentration of water vapor for the subsequent dehydration process is fairly low: typically 8-15% w/w. At a low vapor feed concentration of water, the adsorption equilibrium falls into a linear range of the isotherm. For example, the isotherm of water adsorption on cornmeal for ethanol vapor feed concentrations of 85-95.2% wt% is well represented by a linear correlation[5]. Numerous other studies also have presented a linear isotherm of water sorption on polysaccharide adsorbents for various low humidity feed[2,9-11].

In the linear range of an adsorption isotherm, the equilibrium adsorption is described as following, similar to Henry's law:

$$q = K \cdot C \quad (2)$$

in which q is the mass of water adsorbed per mass of adsorbents (mg water/g dry adsorbent), C is the water vapor concentration (mg water/cm$^3$), and K is linear adsorption equilibrium constant (cm3/g dry adsorbent).

Figure 3:
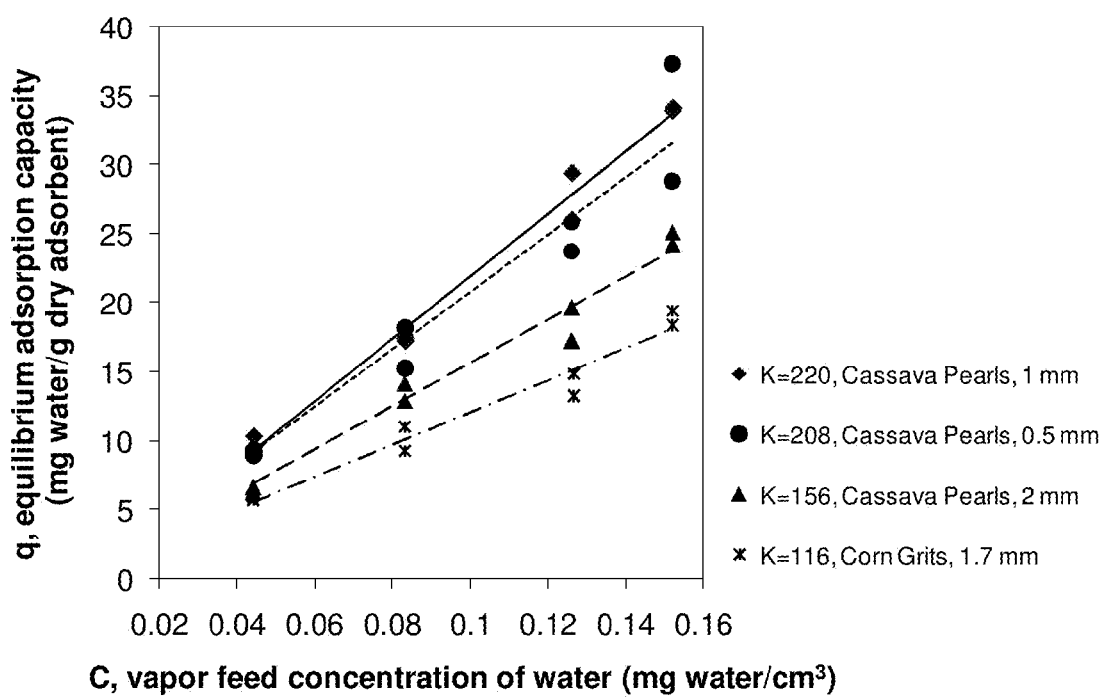
FIG. 3 depicts linear adsorption equilibrium curves for cassava pearls and corn grits adsorbents.

The adsorption equilibrium isotherm of cassava pearls and corn grits in the dilute region is illustrated in FIG. 3. The vapor feed concentration of water in FIG. 3 corresponds to a liquid feed of 88-97% w/w ethanol. At each concentration, duplicate runs were made. Lines represent linear regression of the data points, all of which gave over 0.92 Pearson's coefficient of regression ($r^2$). The constant K was found to be the highest for 1 mm particle size cassava pearls among the three different size pearls tested. The 1 mm pearls resulted in 40% higher water adsorption capacity than the 2 mm size pearls. However, K for the smallest particle size tested (0.5 mm) was slightly lower than or very close to the 1 mm mesh.

Figure 4:
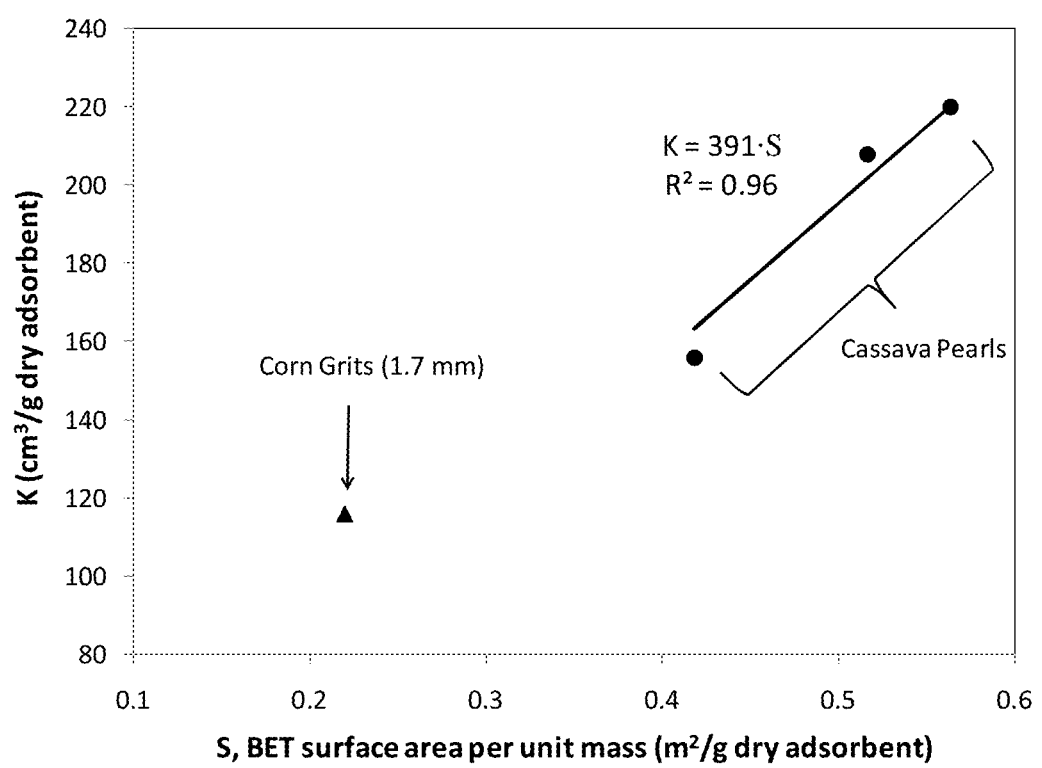
FIG. 4 shows a plot of constant K (linear adsorption equilibrium constant) versus measured BET surface area of cassava pearls per unit mass. Numbers are average of duplicate runs.

The linear adsorption equilibrium constant K was found to correlate linearly with the measured BET specific surface area as illustrated in FIG. 4. The linear regression for the cassava pearls gave over 0.96 Pearson's coefficient of regression ($r^2$). This result indicates that that adsorption equilibrium capacity of cassava pearls is strongly dependent on specific surface area, rather than just the mass of starch adsorbent. The specific surface area can be related to available water adsorption sites of the adsorbents. The high dependence of adsorption equilibrium capacity of the starch pearls on the specific surface area seems to originate from limited access of water molecules inside pearls due to low porosity and the gelatinized/retrograded core of the starch pearls.

Equilibrium water loading for corn grits having an average particle size of 1.7 mm was lower than all cassava pearls tested (FIG. 3). The BET surface area of 1-2 mm diameter corn grits is 0.22 m$^2$/g [27]. The lower water sorption capacity of corn grits could be also related to its lower surface area compared to that of an equivalent size of cassava pearls as represented in SEM images in FIG. 2. Any compositional difference may also contribute to this difference. While the cassava pearls contain close to 100% starch because they are made of cassava starch flour, the corn grits contain other components, such as protein and oil, which are less effective than starch in terms of adsorbing water molecules. Typical corn grits contain approximately 90% starch and 10% protein and other components[27]. Protein, for example, bovine serum albumin, adsorbs water much weakly than polysaccharides such as starch or cellulose[31]. Approximately 40-50% of endosperm protein in corn is known to be zein, which exhibit poor solubility in water due to its high non-polar amino acid content[32,33].

Studies have shown that only a small portion of the potential adsorption sites of starch materials are utilized as most of the water sorption sites are embedded in the interior of the starch matrix into which water must diffuse for the adsorption to occur[26,34]. This means that water loading for starch-based adsorbents is limited to the number of loading sites that are accessible to water molecules. While use of particulate starch would give the maximum water sorption capacity, this would not be practical in a commercial scale due to significant pressure increase over the bed of starch. In this sense, the structural design of cassava pearl provides several advantages. The center core of cassava pearls serves as a supporting scaffold for aggregating immobilized starch particulates on the external surface, providing a mechanical stability to the individual particle. The size of the cooked center can be readily controlled during the pearl production process to provide a different particle diameter of the sorbents. Increased accessible surface area could be readily achieved by manipulating the coating and fixation procedure of starch particulates on the core to give a thicker shell of starch agglomerates with high internal pores.

Operational Adsorption Capacity of Cassava Pearl-Shaped Adsorbents

Separation of water from alcohol in a fixed bed adsorber is a kinetically-controlled process in which water adsorption occurs much faster than that of ethanol[4,5,26,35] Differences in the adsorption rate of water and ethanol on starch-based adsorbents originates from the stronger interaction of water molecules with hydroxyl groups of starch than of ethanol, resulting in a difference in mass transfer rate. The rate of ethanol adsorption is 100-1000 times slower than water adsorption at a given temperature[26].

The diffusion rate of water through starch materials is known to be relatively slow[34]. Under equilibrium adsorption conditions, which are established only when sufficient contact time of water with starch is given, the water molecules can penetrate the intrastarch hydrogen bonds in the starch matrix, maximizing the water load on the adsorbents[17]. A diffusion gradient created throughout the adsorbent allows kinetically-controlled water adsorption. Ethanol adsorption could become significant if contact time is too long, lowering the selectivity of adsorption of water over ethanol.[14,36] However, in a practical packed-bed adsorption system, the adsorption process never reaches equilibrium and is stopped at the breakthrough point to yield a dry ethanol of 99.5% wt. Before the breakthrough point, adsorption on the surface of the starch particle becomes the dominant factor determining the kinetic selectivity of water molecules and operational water adsorption capacity. Studies have shown that extent of water adsorption and selectivity increases as the particle size of the adsorbent decreases.[14,17,33] Smaller particles have higher external surface area and establish a more rapid equilibrium of water sorption than larger particles.

Figure 5:
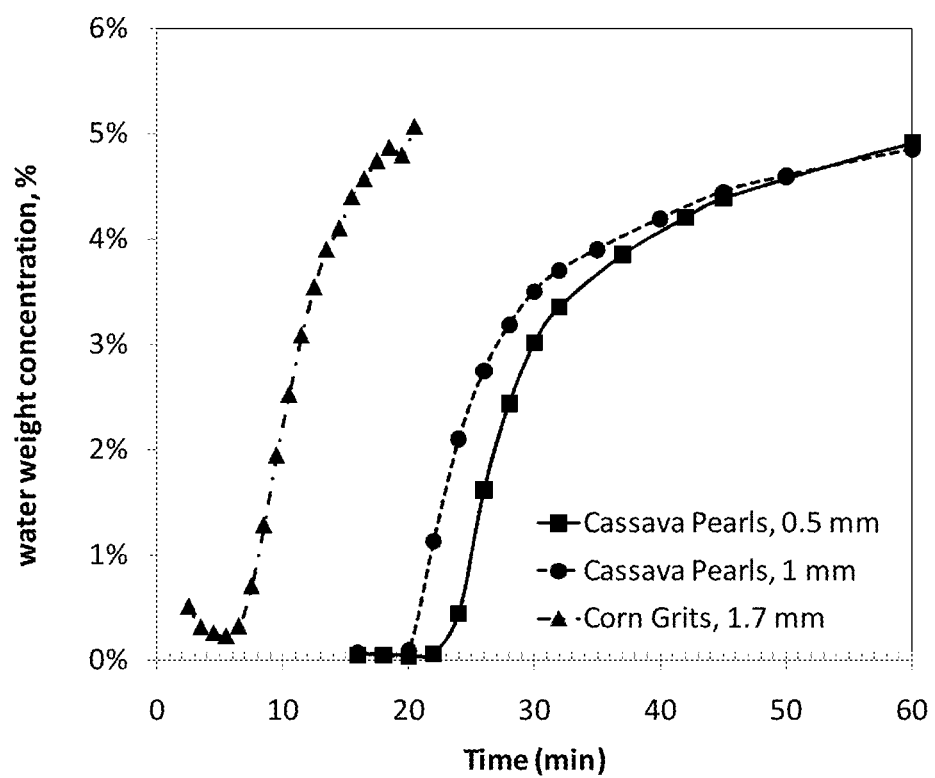
FIG. 5 shows breakthrough curves of cassava pearls (0.5 mm, 1 mm in diameter) and corn grits (1.7 mm diameter) adsorbents. Feed ethanol concentration: 93.6% w/w.

Breakthrough curves of a full 6 ft fixed bed of corn grits having an average diameter of 1.7 mm and cassava pearls of 1 mm and 0.5 mm diameter are presented in FIG. 5 for a feed of 93.7% w/w ethanol. The data represents an average of duplicate runs. The x-axis was adjusted so that the graph highlights the adsorption wavefront, rather than showing the entire adsorption curve until it reaches an equilibrium product concentration. Detailed run conditions are given herein before under Methods. Sorption conditions were identical for all breakthrough runs. The breakthrough point is defined as a time that the product stream contains more than 0.5% w/w water. There was a delay of about 1.5 min between the start of pumping the vapor feed into the column and collecting the first drop of condensate. The time in FIG. 5 represents an elapsed time from the start of the feed cycle. As shown in FIG. 5, the breakthrough time was 7.5 min for corn grits and it was 22 min and 24 min for 1 mm pearls and 0.5 mm pearls, respectively. Corn grits had a significantly shorter breakthrough time, which was expected from the discoveries provided herein given the smaller surface area and lower equilibrium adsorption capacity of corn grits compared to those of cassava pearls FIG. 3 and FIG. 4).).

The operational adsorption capacity at a point of breakthrough and the equilibrium adsorption capacity of the 6 ft bed of cassava pearls are summarized in Table 2.

TABLE 2

Operational adsorption capacity and separation factor at breakthrough point for cassava pearls. Numbers are average of duplicate runs.

| | Adsorption capacity at breakthrough (mg/g) | | separation factor | Equilibrium adsorption capacity (mg/g) | | separation factor |
|---|---|---|---|---|---|---|
| | Water | Ethanol | | Water | Ethanol | |
| Cassava pearls $D_P = 1$ mm | 15.2 | 5.4 | 47.9 | 25.8 | 6.8 | 63.6 |
| Cassava pearls $D_P = 0.5$ mm | 16.4 | 5.2 | 53.0 | 26.5 | 12.2 | 36.5 |

The selectivity of adsorbent was compared by a separation factor which is defined according to the following[36] equation:

$$\alpha = \frac{X_w/X_e}{Y_w/Y_e} \qquad (3)$$

where $X_w$ and $Y_w$ are the mass fractions of water in the sorbed phase and vapor phase at equilibrium, respectively, and $X_e$ and $Y_e$ are the corresponding ethanol mass fractions. Both sizes of pearls resulted in a very similar operational capacity for water. The equilibrium adsorption capacity represents a maximum water loading at given conditions. Water loading at the breakthrough point was nearly 60% of the equilibrium water loading.

At breakthrough, both water and ethanol sorption capacities were not significantly different between the two particle sizes of pearls. The smaller 0.5 mm pearls gave a slightly higher sorption capacity for both water and ethanol than the 1 mm pearls, which was also indicated from the breakthrough profiles. Due to its smaller diameter, the 0.5 mm pearls have less mass transfer constraints than 1 mm particles, which could explain the slightly greater water sorption for the 0.5 mm particles at the breakthrough point. Similarly, the selectivity of water to ethanol at breakthrough, as indicated by the separation factor, was similar for both 0.5 mm and 1 mm pearls with the indicated differences being considered insignificant and within the error limits.

However, at equilibrium, the ethanol loading for 0.5 mm pearls was nearly twice that for 1 mm particles, resulting in a greater separation factor for the 1 mm pearls. It should be noted that although the system reached equilibrium in terms of water sorption, ethanol adsorption might have not reached equilibrium as it takes much longer than water to reach equilibrium.[5,35] Also, water sorbed at equilibrium can further attract ethanol, extending the time required for ethanol to reach equilibrium state. Taking these into consideration, the results still showed the selectivity for water decreased over adsorption contact time for the smaller particles size cassava pearls. The same trends were also observed from the 1 ft bed of pearls used for equilibrium studies as depicted in FIG. 3. At all feed water concentrations tested, the amount of desorbed ethanol was more for the smallest (0.5 mm) pearls than the other two larger sizes of pearls (data not shown). This could be explained by recognizing that gelatinized/retrograded portion of the starch particle is much less selective for water. As shown in the SEM images in FIG. 2, the 0.5 mm pearls were small enough to be close to its gelatinized/retrograded core, displaying mostly smooth external surface, thus having a less BET surface area than expected. Crawshaw and Hills (1990)[36] have reported that cooked corn has a slightly greater total sorption capacity but much less selectivity for water than uncooked grits at equilibrium. For tapioca pearls, the lower selectivity for water due to gelatinization seemed to be negligible up to a breakthrough point, as suggested from the similar separation factor calculated for both pearls in Table 2. At breakthrough, the separation factor of 0.5 mm pearls was similar to that of 1 mm particles, while it was 43% lower at equilibrium.

As for comparison between cassava pearls and corn grits, significant differences in water sorption capacity were observed at both breakthrough and equilibrium. The separation factor for corn grits was not calculated as desorbed ethanol from corn grits adsorption runs were not measured herein. However, Chang et al. (2006)[5,6] have reported a separation factor in a range of 10-30 at equilibrium for a bed of cornmeal adsorbent with a granularity of <0.45 mm for various feed ethanol concentration ranging from 80 to 97% wt and operating temperatures of 82-100° C. Also, Crawshaw and Hills (1990)[36] have shown that various corn starchy materials at equilibrium resulted in a separation factor from 10 and 35 at feed vapor concentrations between 88 to 96% wt ethanol. Despite different conditions and apparatus used in these studies, corn based starch seemed to give a separation factor somewhere between 10 and 35, which is surprisingly and significantly lower than observed for cassava pearls in this study.

Desorption Profiles

Adsorbent regeneration is important to ensure the product dryness in the subsequent adsorption cycle. Bed regeneration in this disclosure was carried out by 105° C. dry $CO_2$ flowing counter-current direction to the feed flow. There are two main advantages of passing the regenerating gas stream in the counter-current direction to that for adsorption: (1) heat of adsorption stored in the upper part of the bed is carried along with the regenerant gas toward more saturated regions, providing additional heat to drive off the adsorbed water; and (2) re-adsorption of water during the regeneration is minimized by carrying the desorbed water molecules from less to more saturated portions of the bed[2]. In this disclosure, the bed regeneration was initiated at breakthrough points for the respective particle size of the cassava pearls. Desorption profiles for 0.5 and 1 mm pearls were compared to see if there are significant difference in desorption rate between these two difference size particles.

Figure 6A:
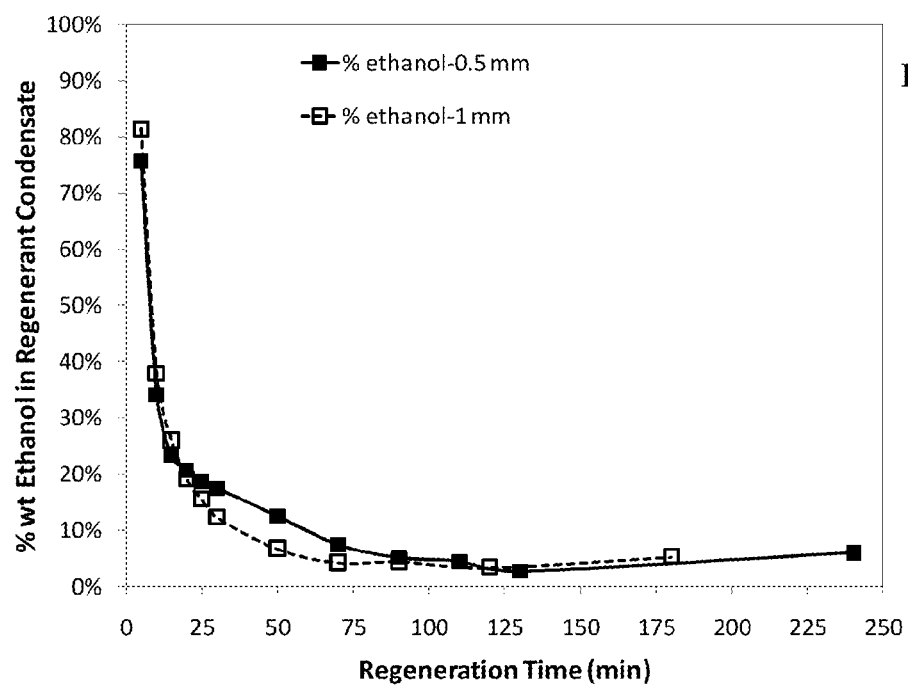
FIGS. 6A and 6B show: (6A) Ethanol wt % in regenerant condensate for tapioca pearls and; (6B) water and ethanol mass desorbed per gram dry adsorbents for the same.
Figure 6B:
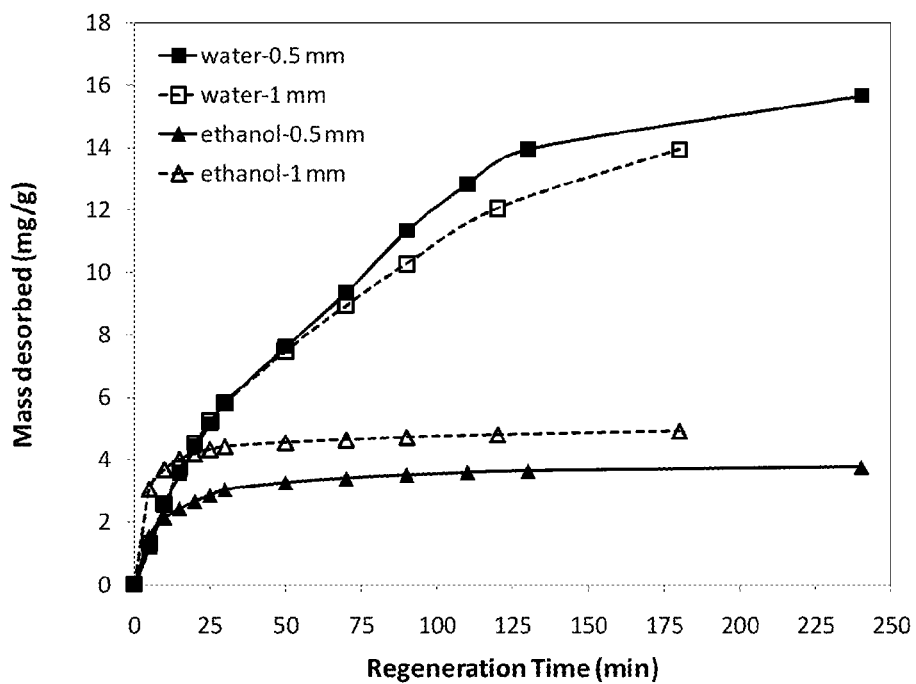

The regeneration effluent composition and desorption profiles are shown in FIGS. 6A and 6B. The desorbed water and ethanol in mg per gram dry adsorbent in FIG. 6B is after subtracting water and ethanol vapor present in the void space of the bed at the initiation of regeneration cycle. The majority of the initial regenerant condensate collected represents the ethanol vapor present in the void fraction of the bed which is carried out first by using the regenerant $CO_2$ gas. Therefore, the first collection is the highest in ethanol content. Approximately after an hour of regeneration, water became the major component comprising more than 90% of the condensate. This means that most of ethanol in the regeneration effluent can be recovered from the first hour of the regeneration.

The mass of water and ethanol desorbed per unit mass of dry pearls is presented in FIG. 6A. There was no significant difference between the 0.5 mm and 1 mm particles in terms of rate of water and ethanol desorption. The mass of desorbed ethanol did not increase beyond 25 min of the regeneration, implying that most of the ethanol is desorbed during the first 25 min, while water desorption took place at a much slower rate than that of ethanol. Another observation was that the 0.5 mm pearls gave off less amount of ethanol than 1 mm particles, despite the similar operational ethanol sorption capacity between the two particle sizes as shown in Table 2. At the end of the 3 hr regeneration, only 75% of the sorbed ethanol was recovered in the regeneration effluent of 0.5 mm pearls, while 92% was recovered for 1 mm pearls. The lower recovery of sorbed ethanol from the 0.5 mm pearls compared to the 1 mm particles, despite the expected mass transfer advantages of smaller particles diameter, could be explained by stronger affinity for ethanol (lower selectivity for water) of cooked starch. As for water desorption, 93% of the sorbed water was recovered after 3 hr regeneration for both particle sizes. The residual water and ethanol in the system required excessive regeneration time to desorb. The desorption rate appeared to be greatly slower than adsorption rate.

Westgate and Ladisch (1993)[26] have related the difference in adsorption and desorption rate to trapping mechanisms. During adsorption, water molecules penetrate the starch matrix making the starch granules swollen. The swelled starch structure starts to shrink during desorption, thereby trapping some of adsorbates.[26,37] Hence, desorbing of the trapped adsorbates would take an excess amount of time and energy. The incomplete recovery of sorbed water and ethanol could be attributed to the entrapment of adsorbates in the starch matrix.

Experimental Summary and Conclusions

Spherical shaped cassava starch is commercially available in various sizes with s narrow particle size distribution. Drying of an alcohol-water mixture of 88-97% w/w ethanol by cassava starch spherical pellets was tested in a fixed bed apparatus. Scanning electron microscopy (SEM) revealed that spherical pellets of cassava starch are constructed from a pre-gelatinized core with negligible internal pore structure, upon which dry starch granules are aggregated. Patches of dry starch aggregates on the shell of the pellets appeared to determine water adsorption capacity of the adsorbent. The adsorption isotherms at 90° C. showed that equilibrium water sorption capacity is strongly related to BET surface area of the adsorbent. The findings indicate that starch adsorbent's performance could be further improved by increasing the accessible surface area per unit mass. Starch gelatinization and retrogradation should be minimized because such processes lead to reduced selectivity for water during adsorption. The drying capacities of spherical pellets of cassava starch was superior to the corn grits, despite their similar particle size, which as disclosed herein, is attributed to greater surface are of the cassava starch pearls than corn grits as well as the compositional differences described.

While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected. As well, those of ordinary skill in the pertinent art will recognize that features that are disclosed as options for use in particular embodiments herein will also be options for use in other embodiments herein, such features including but not limited to features relating to the size or average size (e.g. diameter) of starch pearls and/or their associated crystalline starch granules when used for dehydration processing, and conditions of processing such as liquid or vapor phase, temperatures, and others as disclosed herein.

Literature Cited

Each of the following references and all other references cited in this application is hereby incorporated by reference in its entirety as if individually incorporated by reference and fully set forth.

1. Ladisch, M. R.; Dyck, K. Dehydration of ethanol: new approach gives positive energy balance. *Science* 1979, 205, 898
2. Ladisch, M. R.; Voloch, M.; Hong, J.; Bienkowski, P. R.; Tsao, G. T. Cornmeal adsorber for dehydrating ethanol vapors. *Ind. Eng. Chem. Proc. DD.* 1984, 23, 437.
3. Huang, H.; Ramaswamy, S.; Tschirner, U. W.; Ramarao, B. V. A review of separation technologies in current and future biorefmeries, *Sep. Sci. Technol.* 2008, 62, 1.
4. Crawshaw, J. P.; Hills. J. H. Experimental determination of binary sorption and desorption kinetics for the system ethanol, water, and maize at 90° C. *Ind. Eng. Chem. Res.* 1992, 31, 887.
5. Chang, H.; Yuan, X.; Tian, H.; Zeng, A. Experimental study on the adsorption of water and ethanol by cornmeal for ethanol dehydration. *Ind. Eng. Chem. Res.* 2006a, 45, 3916.
6. Chang, H.; Yuan, X.; Tian, H.; Zeng, A. Experiment and prediction of breakthrough curves for packed bed adsorption of water vapor on corn meal. *Chem. Eng. Prog.* 2006b, 45, 747.
7. Sair, L.; Fetzer, W. R. Water sorption by starches. *Ind. Eng. Chem.* 1944, 36, 205.
8. Rebar, V.; Fischbach, E. R.; Apostolopoulos, D.k Kokini, J. L. Thermodynamics of water and ethanol adsorption on four starches as model biomass separation systems. *Biotechnol. Bioeng.* 1984, 26, 513.
9. Lee, J. Y.; Ladisch, M. R. Polysaccharides as adsorbents—an update on fundamental properties and commercial prospects. *Ann. NY Acad. Sci.* 1987, 506, 491.
10. Westgate, P. J.; Lee, J. Y.; Ladisch, M. R. Modeling of equilibrium sorption of water vapor on starch materials. *T. ASAE.* 1992, 35, 213.
11. Neuman, R. N.; Voloch, M.; Bienkowski, P. R.; Ladisch, M. R. Water sorption properties of a polysaccharide adsorbent. *Ind. Eng. Chem. Fund.* 1986, 25, 422.
12. Beery, K.; Gulati, M.; Kyam, E. P.; Ladisch, M. R. Effect of enzyme modification of corn grits on their properties as an adsorbent in skarstrom pressure swing cycle drier. *Adsorption.* 1998, 4, 321.
13. Ladisch, M. R.; Voloch, M.; Hong, J.; Bienkowski, P.; Tsao, G. T. Cornmeal adsorber for dehydrating ethanol vapors. *Ind. Eng. Chem. Process Des. Dev.* 1984, 23, 437.
14. Hassaballah, A. A.; Hills, J. H. Drying of ethanol vapors by adsorption on corn meal. *Biotechnol. Bioeng.* 1990, 35, 598.
15. Hills, J. H.; Pirzada, I. M. Analysis and prediction of breakthrough curves for packed bed adsorption of water vapour on corn-meal. *Chem. Eng. Res. Des.* 1989, 67, 442.
16. Vareli, G. D.; Demertzis, P. G.; Akrida-Demertzi, K. Water and ethanol adsorption on starchy and cellulosic substrates as biomass separation systems. *Z. Lebensm. Unters. Forsch. A.* 1997, 205, 204.
17. Anderson, L. E.; Gulati, M.; Westgate, P. J.; Kvam, E. P.; Bowman, K.; Ladisch, M. R. Synthesis and optimization of a new starch-based adsorbent for dehumidification of air in a pressure-swing dryer, *Ind. Eng. Chem. Res.* 1996, 35, 1180.
18. Carmo, M. J.; Adeodato, M. G.; Moreira, A. M.; Parente Jr., E. J. S.; Vieira, R. S. Kinetic and thermodynamic study on the liquid phase adsorption by starchy materials in the alcohol-water system. *Adsorption.* 2004, 10, 211.
19. Clay, J. W. *World agriculture and the environment: a commodity-by-commodity guide to impacts and practices*; Island Press: Washington D.C., 2004.
20. Hoover, R. Composition, molecular structure and physicochemical properties of tuber and root starches: a review. *Carbohydr. Polym.* 2001, 45, 253.
21. Rickard, J. E.; Asaoka, M.; Blanshard, J. M. V. Review: The physico-chemical properties of cassava starch. *Trop. Sci.* 1991, 31, 189.
22. Food and agricultural organization (FAO website), Food outlook, No. 2. 2004.
23. Collado, L. S.; Corke, H. Pasting properties of commercial and experimental starch pearls. *Carbohydr. Polym.* 1998, 35, 89.
24. Xu, A.; Seib, P. A. Structure of tapioca pearls compared to starch noodles from mung beans. *Cereal Chem.* 1993, 70, 463.
25. Radley, J. A., Ed.; *Starch Production Technology*; Applied Science Publishers Ltd.: London, 1976.
26. Westgate, P. J.; Ladisch, M. R. Air drying using corn grits as the sorbent in a pressure swing adsorber. *AIChE J.* 1963, 39, 720.
27. Beery, K. E.; Ladisch, M. R. Chemistry and properties of starch based dessicants. *Enz. Microbiol. Tech.* 2001, 28, 573.
28. Beery, K. E.; Ladisch, M. R. Adsorption of water from liquid-phase ethanol-water mixtures at room temperature using starch-based adsorbents. *Ind. Eng. Chem. Res.* 2001, 40, 2112.
29. Cui, S. W., Ed.; *Food carbohydrates: chemistry, physical properties, and applications*; CRC Press: Boca Raton, 2005.
30. Hui, Y. H., Ed.; *Handbook of food science, technology, and engineering*; CRC Press: Boca Raton, 2006.
31. Hong, J.; Voloch, M.; Ladisch, M. R.; Tsao, G. T. Adsorption of ethanol/water mixtures by biomass materials. *Biotechnol. Bioeng.* 1982, 24, 725.
32. Lorenz, K. J.; Kulp, K., Ed.; *Food science and technology* Vol. 41 Handbook of cereal science and technology; Marcel Dekker: New York, 1991.
33. Vareli, G. D.; Demertzis, P. G.; Akrida-Demertzi, K. Effect of adsorbent particle size and temperature on water-ethanol separation by starchy and cellulosic substrates. *Z. Lebensm. Unters. F. A.* 1998, 207, 122.
34. Hanson, T. P.; Cramer W. D.; Abraham, W. H.; Lancaster, E. B. Rates of water vapor absorption in granular corn-M starch. *Chem. Eng. Progr. Symp.* 1971, 67, 35.
35. Lee, J. Y.; Westgate, P. J.; Ladisch, M. R. Water and ethanol sorption phenomena on starch. *AIChE J.* 1991, 37, 1187.
36. Crawshaw, J. P.; Hills. J. H. Sorption of ethanol and water by starchy materials. *Ind. Eng. Chem. Res.* 1990, 29, 307.
37. Hellman, N. N.; Boesch, T. F.; Melvin, E. H. Starch granule swelling in water vapor sorption. *J. Am. Chem. Soc.* 1952, 74, 348.
38. Brunauer, Emmett and Teller. Adsorption of Gases in. Multimolecular Layers. *J. Am. Chem. Soc.* 1938, 60, 309-319.

The invention claimed is:

1. A method of dehydrating an ethanol water mixture comprising,
   a. contacting an ethanol:water mixture of at least 80% w/w ethanol with a first end of a column containing a bed of spherically shaped pearled starch particles; and
   b. removing a dehydrated ethanol product of at least 99% ethanol from a second end of the column.

2. The method of claim 1 further comprising regenerating the bed of pearled starch particles in the column by contacting the second end of the column with $CO_2$ heated to at least 105° C. and collecting water and residual ethanol from the first end of the column.

3. The method of claim 1 wherein the bed of spherically shaped pearled starch particles have a water content of 10% or less prior to being contacted by the ethanol:water mixture.

4. The method of claim 1 wherein the ethanol:water mixture is in a vapor phase when contacting the bed of spherically shaped pearled starch particles.

5. The method of claim 1 wherein the bed of spherically shaped pearled starch particles has a temperature of 90-110° C. when the ethanol:water mixture is contacted with the bed and/or wherein the ethanol:water mixture is in a vapor phase at a temperature of about 100-110° C. when contacting the bed of spherically shaped pearled starch particles.

6. The method of claim 1 wherein:
the spherically shaped pearled starch particles have a BET surface area of 0.4-0.6 m²/g; or
the spherically shaped pearled starch particles have an equilibrium absorption capacity of 6.5-12.5 mg/g, for ethanol and 25-27 mg/g for water.

7. The method of claim 1, wherein:
the pearled starch particles are pearled starch particles having a nominal diameter of 0.2-3 mm having a surface that is at least partially gelatinized and that includes a regular distribution of crystalline starch granules nominally 5-10 microns in diameter over the surface.

8. The method of claim 1, wherein the spherically shaped pearled starch particles have an average nominal diameter of 0.2-3 mm.

9. The method of claim 1, wherein the spherical shaped pearled starch particles are tapioca pearl starch particles.

10. A method of dehydrating an ethanol water mixture comprising, contacting an ethanol:water mixture of 88-97% w/w ethanol with a first end of a column bed consisting of spherically shaped pearled starch particles; and
removing a dehydrated ethanol product being at least 99% ethanol from a second end of the column.

11. The method of claim 10 wherein:
the spherically shaped pearled starch particles are tapioca pearl starch particles or corn pearl starch particles.

12. The method of claim 10, wherein:
the pearled starch particles are pearled starch particles selected to have an average nominal diameter of 0.1-4 mm that are characterized as having (i) at least one of a gelatinized or gelatinized and retrograded starch core, and (ii) the core being surrounded by an aggregate of crystalline starch granules nominally 2-15 microns in diameter.

13. The method of claim 10, wherein the spherically shaped pearled starch particles have an average nominal diameter of 0.2-3 mm.

14. The method of claim 10, wherein the spherical shaped pearled starch particles are tapioca pearl starch particles.

15. A method for dehydrating a mixed vapor containing ethanol and at least 3% by weight water, comprising:
contacting the mixed vapor with starch pearls under conditions effective to dehydrate the mixed vapor to produce an ethanol vapor constituted at least 99% by weight ethanol; and
condensing the ethanol vapor to produce a liquid product constituted at least 99% by weight ethanol.

16. The method of claim 15, wherein the starch pearls have a substantially gelatinized core and a surface populated with crystalline starch granules.

17. The method of claim 16 wherein:
the granules have an average nominal diameters diameter of about 2 to about 15 microns; and
the starch pearls have an average nominal diameter of about 0.2 to about 3 mm.

18. The method of claim 15, wherein said contacting is effective to provide a water:ethanol equilibrium separation factor of greater than 35.

19. The method of claim 15, wherein about 90% or more of the starch pearls have a maximum particle dimension within 20% of the average maximum dimension of the starch pearls.

20. The method of claim 15, wherein:
the starch pearls are comprised about 98% to 100% by weight of starch.

21. The method of claim 15, wherein the starch pearls comprise cassava starch.

22. The method of claim 21, wherein the starch of the starch pearls consists of cassava starch.

23. The method of claim 15, wherein the starch pearls have an average nominal diameter of 0.2-3 mm.

24. The method of claim 15, wherein the starch pearls are tapioca starch pearls.

25. A method for producing ethanol, comprising:
fermenting a medium to produce an aqueous fermentation broth containing ethanol and water;
distilling the fermentation broth to produce a mixture containing ethanol and water; and
dehydrating the mixture by contacting a vapor of the mixture with starch pearls so as to adsorb water on the starch pearls.

26. The method of claim 25, wherein the starch pearls have an average nominal diameter of about 0.2 to about 3 mm.

27. The method of claim 25, wherein said vapor has a temperature in the range of about 100° C. to about 110° C.

28. The method of claim 25, wherein:
the starch pearls have an average nominal diameter in the range of about 0.5 to 1 mm; and
said dehydrating is effective to provide a water:ethanol separation factor at equilibrium of greater than 35.

29. The method of claim 25, wherein the starch pearls are comprised about 98% to 100% by weight of starch.

30. The method of claim 25, wherein the starch pearls comprise cassava or corn starch.

31. The method of claim 25, wherein the starch pearls have an average nominal diameter of 0.2-3 mm.

32. The method of claim 25, wherein the starch pearls are tapioca starch pearls.

\* \* \* \* \*